(12) United States Patent
Leijssen

(10) Patent No.: US 12,130,003 B2
(45) Date of Patent: Oct. 29, 2024

(54) ANTI-FOULING LIGHT EMITTING UNIT FOR MARINE VESSEL SURFACES

(71) Applicant: KONINKLIJKE PHILIPS N.V., Eindhoven (NL)

(72) Inventor: Jacobus Josephus Leijssen, Waare (NL)

(73) Assignee: Koninklijke Philips N.V., Eindhoven (NL)

( * ) Notice: Subject to any disclaimer, the term of this patent is extended or adjusted under 35 U.S.C. 154(b) by 882 days.

(21) Appl. No.: 17/277,762

(22) PCT Filed: Sep. 18, 2019

(86) PCT No.: PCT/EP2019/075002
§ 371 (c)(1),
(2) Date: Mar. 19, 2021

(87) PCT Pub. No.: WO2020/058333
PCT Pub. Date: Mar. 26, 2020

(65) Prior Publication Data
US 2022/0126958 A1 Apr. 28, 2022

(30) Foreign Application Priority Data
Sep. 20, 2018 (EP) ..................................... 18195677

(51) Int. Cl.
*B63B 59/04* (2006.01)
*A61L 2/10* (2006.01)
(Continued)

(52) U.S. Cl.
CPC ................. *F21V 31/00* (2013.01); *A61L 2/10* (2013.01); *B08B 17/02* (2013.01); *B63B 59/08* (2013.01);
(Continued)

(58) Field of Classification Search
CPC ......... B63B 59/04; B63B 59/08; B08B 17/02; A61L 2/10; A61L 2/08; F21S 41/13; F21W 2107/20
See application file for complete search history.

(56) References Cited

U.S. PATENT DOCUMENTS 5,643,424 A 7/1997 Riffe et al.
7,118,240 B2 * 10/2006 Baarman ................... A61L 2/10
362/86
(Continued)

FOREIGN PATENT DOCUMENTS

CN 101709191 B 8/2011
EP 0631637 B1 1/1995
(Continued)

OTHER PUBLICATIONS

International Search Report and Written Opinion from PCT/EP2019/075002 mailed Mar. 26, 2020.

*Primary Examiner* — Ismael Negron

(57) ABSTRACT

A light emitting unit is configured to be applied to a surface area of a marine vessel and includes at least one light source configured to emit anti- fouling light (e.g., UV light), and two electrically conductive plates. One side of the at least one light source is electrically connected to one of the plates and another side to the electric energy distribution arrangement of the light emitting unit. The plates are arranged to form respective capacitors with an electrically conductive area of, or over, the surface of the marine vessel, the capacitors connected in series through the electrically conductive surface area once the light emitting unit is applied to the surface the marine vessel.

15 Claims, 5 Drawing Sheets

(51) Int. Cl.

| | | |
|---|---|---|
| *B08B 17/02* | (2006.01) | |
| *B63B 59/08* | (2006.01) | |
| *C09D 5/06* | (2006.01) | |
| *C09D 5/16* | (2006.01) | |
| *F21V 23/02* | (2006.01) | |
| *F21V 23/04* | (2006.01) | |
| *F21V 31/00* | (2006.01) | |
| *H02J 50/10* | (2016.01) | |
| *H02J 50/40* | (2016.01) | |
| *F21W 107/20* | (2018.01) | |
| *H02J 50/90* | (2016.01) | |
| *H05B 45/50* | (2022.01) | |

(52) U.S. Cl.
CPC ............... *C09D 5/06* (2013.01); *C09D 5/16* (2013.01); *F21V 23/02* (2013.01); *F21V 23/0442* (2013.01); *H02J 50/10* (2016.02); *H02J 50/402* (2020.01); *A61L 2202/11* (2013.01); *B63B 59/04* (2013.01); *F21W 2107/20* (2018.01); *H02J 50/90* (2016.02); *H05B 45/50* (2020.01)

(56) References Cited

U.S. PATENT DOCUMENTS

| | | | | |
|---|---|---|---|---|
| 9,051,028 | B2 | 6/2015 | Smith et al. | |
| 9,611,016 | B2 * | 4/2017 | Salters | G02B 19/0061 |
| 10,040,525 | B2 * | 8/2018 | Salters | B01J 19/123 |
| 10,227,243 | B2 * | 3/2019 | Chew | B08B 9/027 |
| 10,245,337 | B2 * | 4/2019 | Park | F21V 23/04 |
| 10,364,002 | B2 | 7/2019 | Janssen et al. | |
| 10,413,623 | B2 * | 9/2019 | Bogdanovich | A61L 2/085 |
| 10,436,437 | B1 * | 10/2019 | Usher | F21V 3/06 |
| 10,549,831 | B2 * | 2/2020 | Salters | F28F 3/08 |
| 10,555,388 | B2 * | 2/2020 | Van Delden | H05B 45/40 |
| 11,655,009 | B2 * | 5/2023 | Salters | B63B 59/04 |
| | | | | 114/222 |
| 2013/0334960 | A1 | 12/2013 | Waffenschmidt et al. | |
| 2017/0048934 | A1 | 2/2017 | Sempel et al. | |
| 2017/0190397 | A1 | 7/2017 | Salters et al. | |
| 2019/0008009 | A1 | 1/2019 | Van Delden | |
| 2020/0087799 | A1 * | 3/2020 | Van Delden | B63B 59/04 |

FOREIGN PATENT DOCUMENTS

| | | | | |
|---|---|---|---|---|
| GB | 2040314 A * | 8/1980 | ............. | B08B 17/00 |
| GB | 2385026 A * | 8/2003 | ............. | A01K 79/02 |
| JP | 974975 A | 3/1997 | | |
| WO | 2014060921 A1 | 4/2014 | | |
| WO | 2014188347 A1 | 11/2014 | | |
| WO | 2017108641 A1 | 6/2017 | | |
| WO | 2018069330 A1 | 4/2018 | | |

* cited by examiner

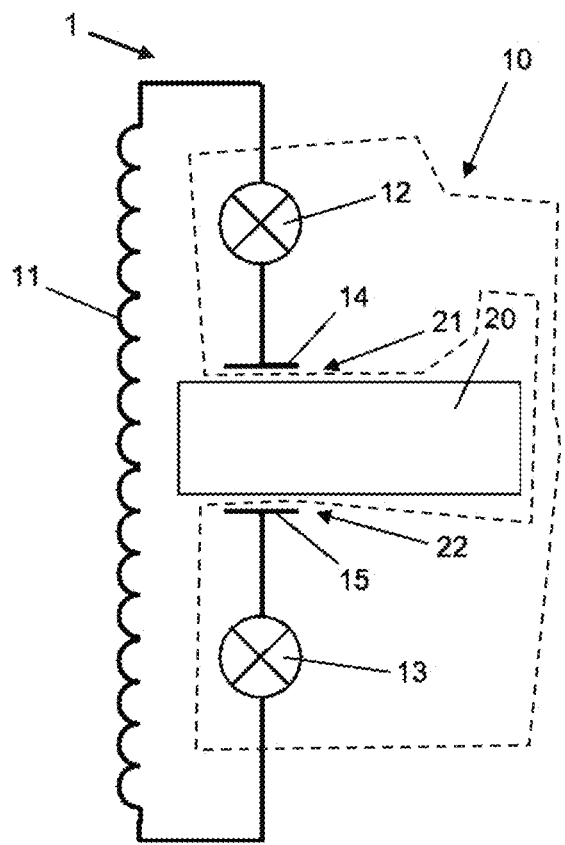
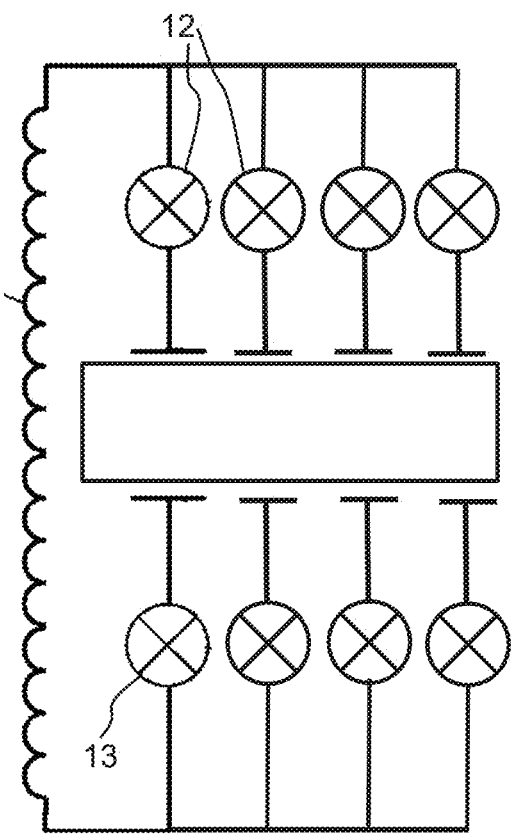
FIG. 1a  FIG. 1b
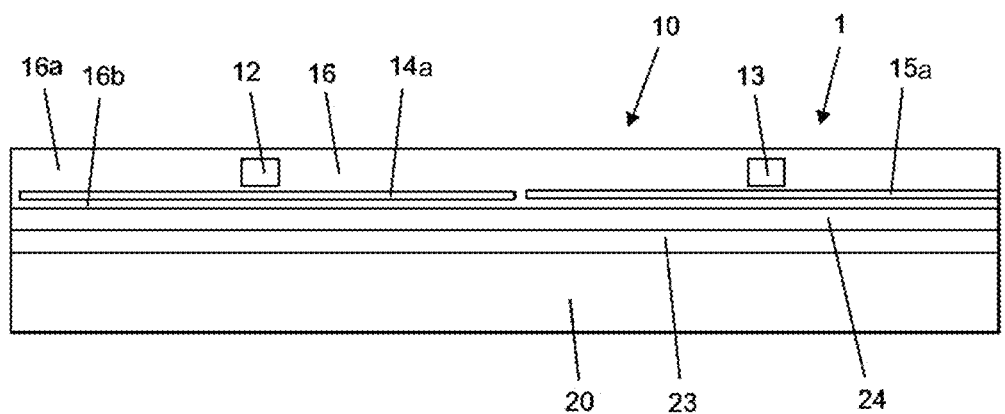
FIG. 2

ANTI-FOULING LIGHT EMITTING UNIT FOR MARINE VESSEL SURFACES

CROSS REFERENCE TO RELATED APPLICATIONS

This application is a U.S. national phase application of International Application No. PCT/EP2019/075002 filed on Sep. 18, 2019, which claims the benefit of EP Application Serial No. 18195677.2 filed on Sep. 20, 2018 and are incorporated herein by reference.

FIELD OF THE INVENTION

In a first aspect, the invention relates to a light emitting unit configured to be applied to a surface area of a marine object, the light emitting unit comprising an electric energy distribution arrangement, and at least one light emitting assembly electrically connected to the electric energy distribution arrangement, including at least one light source configured to emit anti-fouling light.

In a second aspect, the invention relates to an assembly of a holder and a plurality of mechanically interconnected light emitting units of the type as mentioned above.

In a third aspect, the invention relates to a light emitting system comprising at least one light emitting unit of the type as mentioned above, a source of electric power, and an electric power supply element.

In a fourth aspect, the invention relates to an assembly of a marine object and a light emitting system of the type as mentioned above, wherein the electric power supply element and the at least one light emitting unit of the light emitting system are positioned on an electrically conductive surface area of, or over, the marine object.

In a fifth aspect, the invention relates to an assembly of a marine object and at least one light emitting unit of the type as mentioned above, wherein the at least one light emitting unit is positioned on an electrically conductive surface area of, or over, the marine object.

In a sixth aspect, the invention relates to a method of applying a plurality of light emitting units of the type as mentioned above to a surface area of a marine object.

BACKGROUND OF THE INVENTION

Biofouling of surfaces which are exposed to water, during at least a part of their lifetime, is a well-known phenomenon, which causes substantial problems in many fields. For example, in the field of shipping, biofouling on the hull of ships is known to cause a severe increase in drag of the ships, and thus increased fuel consumption of the ships. In this respect, it is estimated that an increase of up to 40% in fuel consumption can be attributed to biofouling.

In general, biofouling is the accumulation of microorganisms, plants, algae, small animals and the like on surfaces. According to some estimates, over 1,800 species comprising over 4,000 organisms are responsible for biofouling. Hence, biofouling is caused by a wide variety of organisms, and involves much more than an attachment of barnacles and seaweeds to surfaces. Biofouling is divided into micro fouling which includes biofilm formation and bacterial adhesion, and macro fouling which includes the attachment of larger organisms. Due to the distinct chemistry and biology that determine what prevents them from settling, organisms are also classified as being hard or soft. Hard fouling organisms include calcareous organisms such as barnacles, encrusting bryozoans, mollusks, polychaetes and other tube worms, and zebra mussels. Soft fouling organisms include non-calcareous organisms such as seaweed, hydroids, algae and biofilm "slime". Together, these organisms form a fouling community.

As mentioned in the foregoing, biofouling creates substantial problems. Biofouling can cause machinery to stop working and water inlets to get clogged, to mention only two other negative consequences than the above-mentioned increase of drag of ships. Hence, the topic of anti-biofouling, i.e. the process of removing or preventing biofouling, is well-known.

WO 2014/188347 A1 discloses a method of anti-fouling of a surface while said surface is at least partially submersed in a liquid environment, in particular an aqueous or oily environment. The method involves providing an anti-fouling light and providing an optical medium in close proximity to the protected surface, the optical medium having a substantially planar emission surface. At least part of the light is distributed through the optical medium in a direction substantially parallel to the protected surface, and the anti-fouling light is emitted from the emission surface of the optical medium, in a direction away from the protected surface. The anti-fouling light may be ultraviolet light, and the optical medium may comprise ultraviolet transparent silicone, i.e. silicone that is substantially transparent to ultraviolet light, and/or ultraviolet grade fused silica, in particular quartz.

By applying the method known from WO 2014/188347 A1, it is possible to cover a protected surface to be kept clean from biofouling, at least to a significant extent, with a layer that emits germicidal light. The protected surface can be the hull of a ship, as mentioned earlier, but the method is equally applicable to other types of surface.

WO 2014/188347 A1 further discloses a lighting module which is suitable to be used for putting the above-mentioned method to practice. Thus, the lighting module comprises at least one light source for generating anti-fouling light and an optical medium for distributing the anti-fouling light from the light source. The at least one light source and/or the optical medium may be at least partially arranged in, on and/or near the protected surface so as to emit the anti-fouling light in a direction away from the protected surface. The lighting module may be provided as a foil which is suitable for application to the protected surface. Such a foil may be substantially size-limited in two orthogonal directions perpendicular to the thickness direction of the foil, so as to provide an anti-fouling tile, in another embodiment the foil is substantially size-limited in only one direction perpendicular to a thickness direction of the foil, so as to provide an elongated strip of anti-fouling foil. In any case, it is possible for the lighting module to comprise a two-dimensional grid of light sources for generating anti-fouling light and for the optical medium to be arranged to distribute at least part of the anti-fouling light from the two-dimensional grid of light sources across the optical medium so as to provide a two-dimensional distribution of anti-fouling light exiting a light emission surface of the light module.

WO 2014/188347 A1 discloses that in embodiments the foil may have a thickness in an order of magnitude of a couple of millimeters to a few centimeters. In this respect, it is noted that it is an object of the invention to provide ultrathin anti-fouling tiles, more generally speaking, ultrathin anti-fouling light emitting units, suitable for arrangement on a ship's hull and other surfaces to be submitted to an anti-fouling action. It is desirable to provide light emitting units having a thickness that is in an order of magnitude of a few millimeters at the maximum, yet comprising light sources and arrangements for distributing electric energy.

SUMMARY OF THE INVENTION

According to the invention, a light emitting unit is provided which is configured to be applied to a surface area of a marine object, and which comprises:

an electric energy distribution arrangement, and at least one light emitting assembly electrically connected to the electric energy distribution arrangement, including at least one light source configured to emit anti-fouling light, and further including two electrically conductive plates, wherein the at least one light source is at the one side electrically connected to one of the electrically conductive plates and at the other side to the electric energy distribution arrangement, and wherein the electrically conductive plates of the at least one light emitting assembly are arranged to constitute respective capacitors with an electrically conductive surface area formed by or over the surface area of the marine object, said capacitors being connected in series through the electrically conductive surface area of the marine object once the light emitting unit is actually applied to a surface area of a marine object.

The invention provides a light emitting unit that is designed in such a way that it is possible to have ultrathin embodiments of the light emitting unit, particularly embodiments in which the light emitting unit extends substantially in two orthogonal directions and has a relatively small dimension in a third direction that is orthogonal to said two orthogonal directions. When the light emitting unit is used as envisaged, namely on a surface area of a marine object, a closed electric circuit is obtained through an electrically conductive surface area (which may be the surface area of the marine object, or a separate conductive later) so that the at least one light source can be provided with electric power. In particular, the electrically conductive plates serve to constitute respective capacitors with the electrically conductive surface area, wherein the capacitors are connected in series through the electrically conductive surface area, without any need for galvanic connection.

In the context of the invention, a first notable advantage of the use of the electrically conductive plates is that the plates can be so thin that they hardly contribute to the thickness of the light emitting unit. Another advantage is that the capacitors which are formed by the plates provide a current limiting function for the at least one light source. However, this is achieved without requiring discrete capacitor components. Thus, the complexity of the light emitting unit is kept to a minimum. It may for example comprise only a conductive layer (which forms the electrically conductive plates and electrical interconnections) and the light source (s).

Further, the capacitors which are formed (for current limiting) avoid the development of heat and any short circuit currents are limited.

In one set of examples, the electrically conductive surface comprises an electrically conductive surface area of the marine object. The light emitting unit is applied directly to the surface area of the marine object. A paint and/or glue layer over the electrically conductive surface area of marine object (e.g. the hull) may function as a capacitor dielectric.

The two conductive plates thus each may be considered to form a capacitor half of a capacitor, wherein the capacitor dielectric is formed by two layers of the paint and/or glue, and the middle of the dielectric includes a galvanically isolated electrically conductive layer (the hull). Considered another way, the two conductive plates may be considered to form first and second capacitors in series, with the junction between them defined by the grounded hull (or other electrically conductive surface area).

In another set of examples, the electrically conductive surface comprises a water layer formed over the surface area of the marine object, for example over the light emitting assembly. This water layer is for example sea water. The surface area of the marine object is again the hull, but it does not need to be electrically conductive in this example. The electrical coupling of the two capacitor halves is achieved by the water layer. The electrically conductive plates may then be at an outer region of the light emitting unit hence nearest the water (rather than at an inner region and hence nearest the hull). The capacitor dielectric is then formed by a material in which the electrically conductive plates are embedded, i.e. the bulk material of the light emitting unit.

The design of the light emitting unit can be realized in such a way that the electric energy distribution arrangement (which may for example be an inductor coil, which forms a secondary side of an inductive energy transfer system, as explained below) and the at least one light emitting assembly can be made to substantially extend in a single sheet, with only a minimum of crossings, wherein crossings are to be understood as areas in the electric energy distribution arrangement where electrically conductive material in the form of tracks or the like needs to be present at two levels in order to enable the electric energy distribution arrangement to extend from and to all positions as necessary for having complete electric energy distribution throughout the light emitting unit.

The at least one light emitting assembly of the light emitting unit may comprise any number of light sources as applicable/desirable. In a practical embodiment of the light emitting unit, the light emitting unit may comprise a plurality of light emitting assemblies, and each light emitting assembly includes two light sources, wherein one light source is at the one side electrically connected to one of the electrically conductive plates and at the other side to the electric energy distribution arrangement, and wherein the other light source is at the one side electrically connected to the other of the electrically conductive plates and at the other side to the electric energy distribution arrangement. On the other hand, it is also possible that the light emitting assembly comprises more than two light sources.

The light source of each light emitting assembly preferably allows current flow in both directions. In one example, the (or each) light source comprises a LED and a parallel protection diode allowing current flow in the opposite direction. The parallel protection diode for example has a forward conduction threshold, for example comprising a Zener diode. In another example, the (or each) light source comprises a pair of parallel back-to-back LEDs.

It follows from the foregoing remarks in respect of the desire to only have minimal thickness of the light emitting unit according to the invention that it is advantageous if the electrically conductive plates of the at least one light emitting assembly are arranged adjacent to each other in the light emitting unit, at a mutual distance. In that way, it can be achieved that all components of the at least one light emitting assembly practically extend in one and the same sheet in the light emitting unit. There may be a single conductive layer, with no cross-overs in the light emitting assembly.

In conformity with what has been suggested earlier, the at least one light emitting assembly may include two light sources, wherein one light source is at the one side electrically connected to one of the electrically conductive plates and at the other side to the electric energy distribution arrangement, and wherein the other light source is at the one side electrically connected to the other of the electrically conductive plates and at the other side to the electric energy distribution arrangement. The two light sources as mentioned may be positioned in such a way in the at least one light emitting assembly that they are opposite in the sense that when alternating current is applied to the light sources, continuous emission of anti-fouling light from the at least one light emitting assembly is obtained, alternatingly from the two light sources.

The light emitting unit according to the invention may be of a layered setup, comprising a layer of electrically conductive material in which both the electric energy distribution arrangement and the electrically conductive plates of the at least one light emitting assembly are included. The layer of electrically conductive material may be provided in any suitable manner, for example as a sheet that has been subjected to cutting actions, i.e. through material removal techniques, or through material addition techniques such as vapor deposition. It may be sufficient for the layer of electrically conductive material as mentioned to have a thickness that is in a range of 3-15 µm. The light emitting unit may further comprise a flexible material in which the layer of electrically conductive material is embedded. The entire light emitting unit may be flexible so as to be capable of closely following any shape of surface area to be covered. In this respect, it is to be noted that the light emitting unit may be designed to cover surface areas of any possible shape, and that use of the invention is possible in both the context of surface areas that are curved/bent and surface areas that are not.

The light emitting unit according to the invention may be made to extend substantially in two orthogonal directions, a dimension of the light emitting unit in a third direction that is orthogonal to said two orthogonal directions being smaller than 2 mm, i.e. may be made to not be thicker than 2 mm.

The electric energy distribution arrangement of the light emitting unit according to the invention may comprise a structure of electrically conductive tracks extending in the light emitting unit. The thickness of the tracks as mentioned only needs to be minimal as compared to other types of electrically conductive components such as wires. Further, manufacturing a structure of tracks can be done in far less complex ways than manufacturing a structure of wires, such as through cutting a structure as desired in a sheet of material or using techniques such as vapor deposition.

The electric energy distribution arrangement for example comprises an inductor coil. This may form a secondary side of a transformer, used for wireless receipt of power from a primary side of the transformer.

The light emitting unit according to the invention may be equipped with a plurality of light emitting assemblies, in which case the electrically conductive plates of the respective light emitting assemblies may be arranged in the light emitting unit in a pattern of rows and columns, which allows for a possibility of the electric energy distribution arrangement comprising electrically conductive tracks extending between the electrically conductive plates of the respective light emitting assemblies in the pattern of rows and columns.

It is practical for the electric energy distribution arrangement of the light emitting unit according to the invention to comprise at least one electric coil. At least one electric coil may be sufficient, but two electric coils may be applied if it is desired to decrease the chance of failure of the light emitting unit in case of damage. The at least one electric coil may be provided in the form of an electrically conductive track laid down in an appropriate, wound configuration.

The light emitting unit according to the invention may comprise a dielectric material, wherein the electric energy distribution arrangement and the at least one light source and the two electrically conductive plates of the at least one light emitting assembly may be embedded in the dielectric material. An example of a dielectric material that may be used in the context of the invention is silicone rubber.

In the at least one light emitting assembly of the light emitting unit according to the invention, the electrically conductive plate to which the at least one light source is at the one side electrically connected may be arranged and configured to reflect anti-fouling light emitted by the at least one light source during operation thereof. In such a way, clever use is made of the presence of the electrically conductive plate, wherein the plate does not only have a function in conducting electric power, but also in promoting light emission from the light emitting unit.

In some examples, the electrically conductive plates are between the light source and the surface of the marine object. Thus, the reflection is away from the surface of the marine object, towards the outer surface of the light emitting unit. In examples, this is the surface requiring anti-fouling protection, since it is the surface in contact with water.

According to an aspect of the invention, it may be practical if the at least one light source is electrically connected to the electric energy distribution arrangement through an electrically conductive member such as a wire or a track, and the electrically conductive plate to which the at least one light source is at the one side electrically connected is provided with a slot for leaving space to the electrically conductive member, the electrically conductive member extending in the slot and being electrically insulated from the electrically conductive plate. This setup represents another measure for having a thickness of the light emitting unit that is as small as possible, as it allows for having the at least one light source, the electrically conductive member for electrically connecting the at least one light source to the electric energy distribution arrangement, and the electrically conductive plate at one and the same level in the light emitting unit.

The at least one light source of the at least one light emitting assembly may be of any suitable type, and may comprise an LED, for example.

As explained in the foregoing, the invention relates to a light emitting unit, and the invention also relates to an assembly of a holder and a plurality of mechanically interconnected light emitting units arranged on the holder, from which the light emitting units are to be taken in a process of applying the light emitting units to a surface area of a marine object. Such a holder may comprise a reel or any other suitable holder/support from which the light emitting units may be taken.

The invention further relates to a light emitting system comprising at least one light emitting unit as defined in the foregoing, a source of electric power, and an electric power supply element, wherein the electric power supply element and the at least one light emitting unit are arranged with respect to each other so as to enable inductive transfer of electric power from the electric power supply element to the at least one light emitting unit, so as to minimize the chance of interruption of electric power supply from the source of electric power all the way to the at least one light emitting unit.

The electric power supply element for example comprises the primary side of a transformer, of which the electric energy distribution arrangement forms the secondary side.

An assembly of a marine object and a light emitting system as mentioned is also included in the invention, particularly an assembly in which the electric power supply element and the at least one light emitting unit of the light emitting system are positioned on a surface area of the marine object. In case the surface area of the marine object is covered with a paint layer, the at least one light emitting unit may be attached to such layer. One example of the marine object is a vessel having a metal hull, in which case the electrically conductive surface area is a surface area of the metal hull. The light emitting system can also be used on a marine object that originally does not include an electrically conductive surface area. In such a case, the marine object may be provided with an electrically conductive layer at one or more appropriate positions, for example, which electrically conductive layer may be a paint layer. It may be advantageous to use paint that is a mixture of commonly available paint and ferrite or another high permeability material. As also mentioned above, the sea water may in other examples be used to form the electrically conductive surface area for a non-conductive hull.

Still further, the invention relates to an assembly of a marine object and at least one light emitting unit, wherein the at least one light emitting unit is positioned on an electrically conductive surface area formed by or over the surface area of the marine object, and also to a method of applying a plurality of light emitting units to an electrically conductive surface area formed by or over the surface area of the marine object, wherein the light emitting units are arranged in a pattern of rows and columns. In conformity with what has been suggested earlier, it is possible that a plurality of interconnected light emitting units is provided on a reel and is taken from the reel which is unwound in the process. The light emitting units may be attached to the surface area of the marine object in any suitable way such as through one of gluing and magnetic attachment.

The above-described and other aspects of the invention will be apparent from and elucidated with reference to the following detailed description of aspects of the theoretical background of the invention and practical ways of putting the invention to practice.

BRIEF DESCRIPTION OF THE DRAWINGS

The invention will now be explained in greater detail with reference to the figures, in which equal or similar parts are indicated by the same reference signs, and in which:

FIGS. 1a and 1b illustrate a basic setups of a light emitting assembly of a light emitting unit according to the invention, arranged on a ship's hull;

FIG. 2 diagrammatically shows a cross-section of a first example of a light emitting unit according to the invention and a portion of a ship's hull on which the light emitting unit is arranged;

DETAILED DESCRIPTION OF EMBODIMENTS

Figure 3:
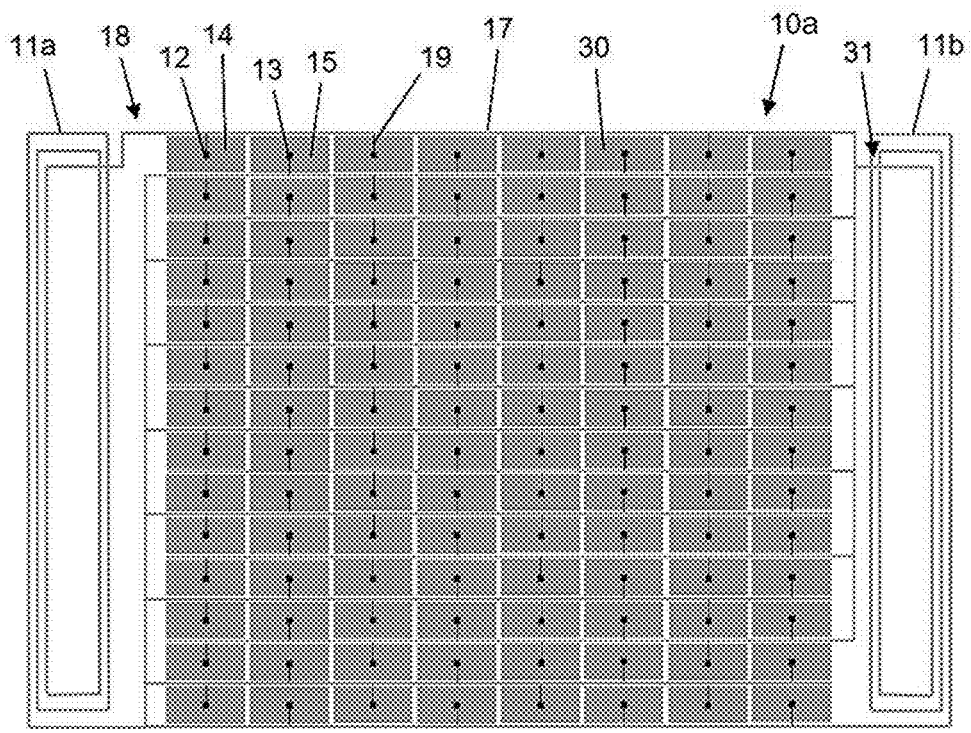
FIG. 3 diagrammatically shows a first possible structure of a metal foil as may be part of a light emitting unit according to the invention, and light sources arranged on the metal foil.

In a general sense, the invention relates to a light emitting unit configured to be applied to a surface area of a marine object, the light emitting unit comprising at least one light source configured to emit anti-fouling light. The anti-fouling light may be UV-C light, for example, which is known for being effective when it comes to anti-fouling so that good results may be achieved. In the following, it is assumed that the marine object is a ship and that the light emitting unit according to the invention is designed to be arranged on the ship's hull, which does not alter the fact that numerous other possibilities are covered by the invention as well.

The light emitting unit according to the invention comprises an electric energy distribution arrangement, and at least one light emitting assembly electrically connected to the electric energy distribution arrangement. In preferred examples, the electric energy distribution arrangement receives power wirelessly, for example by inductive power transfer. Besides the at least one light source for emitting anti-fouling light, the at least one light emitting assembly further includes two electrically conductive plates.

FIG. 1a illustrates a basic setup of such a light emitting assembly 10, wherein it is assumed that the light emitting unit of which the light emitting assembly 10 is part is arranged on a ship's hull 20. In FIG. 1, a coil 11 and two light sources 12, 13 are shown, one light source 12 being positioned between one of the electrically conductive plates 14, 15 and the coil 11, and the other light source 13 being positioned between the other of the electrically conductive plates 14, 15 and the coil 11.

The coil 11 and the electrical conductors between the coil 11 and the light sources 12,13 may be considered to form an electric energy distribution arrangement. However, as a minimum, the electric energy distribution arrangement is a set of conductors for delivering power to the light sources. The combination of the electric energy distribution arrangement 11 and the light emitting assembly 10 is a light emitting unit 1.

As explained earlier, it is possible for the light emitting assembly 10 to comprise just one light source or more than two light sources, whatever is appropriate in a given situation.

The inductive power transfer to the coil 11 is an AC power transfer. In preferred arrangements, the light sources allow current flow in both directions. In one example, each light source 12, 13 comprises a LED and a parallel protection diode such as a Zener diode, allowing current flow in the opposite direction. Such a parallel diode combination is a typical UV-C LED package. In another example, each light source comprises a pair of parallel back-to-back LEDs.

Each light source 12,13 of FIG. 1 may in fact comprise an arrangement of multiple LEDs, in series or parallel or with a combined series and parallel arrangement.

Although in FIG. 1 the electrically conductive plates 14, 15 are schematically shown on opposite sides of the hull, in fact the plates are on the same side (the outside) and they are laterally spaced from each other. The circuit essentially comprises two capacitors in series. A first is defined between the electrically conductive plate 14 and the hull 20 and the second is defined between the electrically conductive plate 15 and the hull 20. Alternatively, the circuit may be considered to comprise two independent sub-circuits from opposite sides of the power supply to ground through a respective light source. The light sources are actuated by opposite phases of the power supply.

The hull may be considered to be the circuit ground. The AC power supply delivered by the electric energy distribution arrangement example has a symmetrical voltage about this circuit ground. The hull is however galvanically isolated from the light sources.

Thus, at one position on the hull 20, a first capacitor 21 is realized by means of a first one of the plates 14, 15 and the hull 20, and at another position on the hull 20, a second capacitor 22 is realized by means of a second one of the plates 14, 15 and the hull 20, the two capacitors 21, 22 being connected in series through the hull 20, assuming that the hull 20 comprises an electrically conductive material, particularly a metal material.

In the capacitors 21, 22, a dielectric material and/or another suitable material may be present between the respective plate 14, 15 and the hull 20. When an alternating current is applied in the circuit as shown, the light sources 12, 13 are powered with a capacitive coupling (to the ground plane), and the capacitors provide current limitation (the current being limited in proportion with the rate of change of voltage). The current is thereby controlled based on the operating frequency. The capacitors do not dissipate significant amounts of power and thus do not heat up. The capacitors for example have a capacitance of the order of hundreds of pF.

There is no galvanic coupling between the light emitting assembly 10 and the hull 20. This is an important aspect in letting the light emitting unit according to the invention be redundant to damage, wherein particularly shorts to the hull 20 can be avoided.

The light sources 12, 13 may be LEDs such as UV-C LEDs as mentioned above. As indicated in FIG. 1a, when a light source 12, 13 is arranged between the coil 11 and one of the plates 14, 15, and another light source 12, 13 is arranged between the coil 11 and another of the plates 14, 15, it is advantageous if the light sources 12, 13 have an opposite orientation so that when a negative voltage is applied, the one light source 12, 13 is activated, whereas when a positive voltage is applied, the other light source 12, 13 is activated. In this way, efficient use of the alternating current is enabled, wherein always one light source 12, 13 is in an active state.

A light emitting unit according to the invention may comprise only one light emitting assembly 10 as illustrated in FIG. 1a. However, in order to be able to cover relatively large surface areas, it is practical to have a plurality of light emitting assemblies 10 in a light emitting unit. In order to have high electric redundancy, which is preferred in the context of light emitting units to be arranged on a ship's hull or the like, in which context impacts on the light emitting units may be expected, various light emitting assemblies 10 may be arranged in parallel between the respective sides of the coil 11.

This is shown in FIG. 1b.

It is possible for the coil 11 and the plates 14, 15 to be realized in a thin layer structure that may be made of metal. In that way, the overall thickness of the light emitting unit can be kept as small as possible. In this respect, reference is made to FIG. 2, in which a cross-section of a light emitting unit 1 and a portion of a ship's hull 20 on which the light emitting unit 1 is arranged is shown.

FIG. 2 relates to a light emitting unit 1 according to the invention, and shows a portion of the light emitting unit 1 and a portion of the hull 20 on which the light emitting unit 1 is arranged. By way of example, a flat appearance of the hull 20 and the light emitting unit 1, i.e. an appearance free from curves/bends, is suggested by means of FIG. 2, but that does not alter the fact that another appearance is possible. As explained earlier, the light emitting unit 1 according to the invention may have any suitable shape for covering all kinds of surface areas.

The light emitting unit 1 comprises at least one light emitting assembly 10 having light sources 12, 13 and electrically conductive plates 14a, 15a as explained earlier with reference to FIG. 1. In the orientation of the light emitting unit 1 as shown, the plates 14a, 15a are arranged adjacent to each other, at a certain level in the light emitting unit 1, and the light sources 12, 13 are arranged above the plates 14a, 15a. Alternatively, the light sources 12, 13 may be at least partially located at the same level as the plates 14a, 15a, in which case the plates 14a, 15a may be provided with a slot or the like for leaving space to the light sources 12, 13 and electrically conductive members connecting the light sources 12, 13 to the electric energy distribution arrangement (i.e. the conducting lines) of the light emitting unit 1. The light sources 12, 13 and the plates 14a, 15a are embedded in a slab 16 of material such as silicone rubber, and the same is applicable to the coil 11 (not shown in FIG. 2) and other components involved in providing and distributing electric energy throughout the light emitting unit 1. In general, by having an embedded configuration of the various electric components of the light emitting unit 1, a fully closed package is obtained, as it were, wherein it is ensured that those components cannot be reached by water from the marine environment in which the light emitting unit 1 is intended to be used.

There is preferably only one conductive layer, which forms the coil 11, electrically conductive plates 14a, 15a and interconnection tracks to the light sources 12, 13. Thus, the light sources may be the only discrete components. The current limiting capacitors are formed without the need for discrete capacitor components.

The plates 14a, 15a may comprise a material having light reflective properties, such as a polished metal material, so that the plates 14a, 15a may not only be used as components of capacitors 21, 22 for providing current limitation and enabling capacitive transfer of electric energy to the light sources 12, 13, but also as reflectors for the light emitted by the light sources 12, 13 during operation thereof.

The reflection is towards the outer surface (opposite the hull) of the light emitting unit 1. This is the surface in contact with the water and hence the surface where protection against biofouling is needed. Thus, light is more effectively transferred to the surface to be treated.

In the light emitting unit 1, the slab 16 of material in which the light sources 12, 13, the plates 14a, 15a and other components are embedded may comprise two layers 16a, 16*b* of different material, which does not alter the fact that the slab 16 of material may comprise a single type of material. A top layer or exterior layer 16*a* may comprise silicone rubber, as mentioned, whereas a bottom layer or interior layer 16*b* may comprise barium titanate or another material that is suitable for increasing capacitance. The bottom layer 16*b* may be entirely made of such other material or may comprise spots/areas where such material is present. The bottom layer 16*b* can be provided on the hull 20 first, after which the other components of the light emitting unit 1 can be provided, or the bottom layer 16*b* can be provided as an integral part of the light emitting unit 1. Having material in the light emitting unit 1 for increasing capacitance may enable having a lower frequency of the alternating current, may decrease capacitance losses, may increase flexibility in the tuning range, allowing for a lower voltage, and/or may allow for using smaller electrically conductive plates 14*a*, 15*a*.

As illustrated in FIG. 2, it is possible for the hull 20 to be covered with a layer 23 of paint, and it is possible for the light emitting unit 1 to be attached to the hull 20 covered with paint through a layer 24 of glue. The paint and/or glue then form part of the dielectric layer of the capacitor, in addition to the layer 16*b*.

Other possibilities are covered by the invention as well: the invention is not limited to one or more types of attachment, and it is not essential whether or not one or more layers are present between the hull 20 and the light emitting unit 1. Preferably, the permittivity and permeability of any layer as may be present between the hull 20 and the light emitting unit 1 are high, at least to such an extent that the functioning of the coil 11 and the quality of the capacitors 21, 22 are not compromised. In general, permittivity and permeability of material as may be present between the hull 20 and the coil 11 and the electrically conductive plates 14*a*, 15*a* of the light emitting unit 1 may be different at different positions, wherein it is practical if the permeability is highest at the position of the coil 11.

In particular, capacitive coupling between the coil 11 and the hull should be kept to a minimum.

Figure 4:
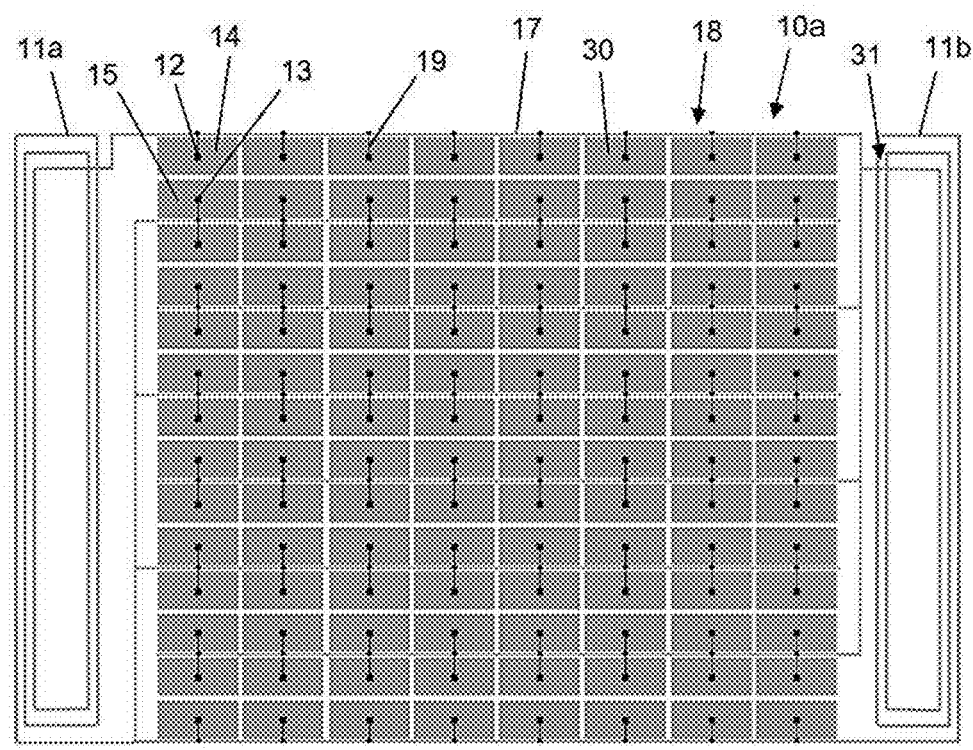
FIG. 4 diagrammatically shows a second possible structure of a metal foil as may be part of a light emitting unit according to the invention, and light sources arranged on the metal foil.

FIGS. 3 and 4 illustrate two possible structures of a metal foil 30 as may be part of a light emitting unit 1, and light sources 12, 13 arranged on the metal foil 30. In both cases, the light emitting unit 1 includes a plurality of light emitting assemblies 10*a* and two coils 11*a*, 11*b*. By having two coils 11*a*, 11*b* instead of just one, it is achieved that if power supply from one coil 11*a*, 11*b* fails, all of the power supply can still be taken care of by the other coil 11*a*, 11*b*, so that the emission of light from the light sources 12, 13 can still take place. The metal foil 30 is shaped such that the coils 11*a*, 11*b* are formed in a foil part as present at two opposite lateral sides of the foil 30, that the plates 14, 15 of the light emitting assemblies 10*a* are formed in a foil part as present between the coils 11*a*, 11*b*, in a pattern of rows and columns, and that electrically conductive tracks 17 of the electric energy distribution arrangement 18 are formed at positions for connecting each of the light sources 12, 13 to the coils 11*a*, 11*b*. The metal foil can be provided as a sheet in which a structure has been made by material removal, or can be realized on the basis of material addition techniques.

The metal foil used to form the conducting lines 17, 19 and plates 14, 15 comprises a single sheet. This is possible because no cross overs are present. The only cross over needed is in the region of the coils 11*a*, 11*b*. The coil area is designed to enable this cross over by having an insulating layer within the structure.

All of the light sources 12 which connect to one side of the coils 11*a*,11*b* are in parallel and all of the light sources 13 which connect to the other side of the coils 11*a*,11*b* are in parallel (as shown in FIG. 1*b*). However, each light source may itself comprise a series connection of multiple LEDs.

Not only does the incorporation of the components as mentioned in a single sheet of foil 30 contribute to keeping the thickness of the light emitting unit 1 to a minimum, but it is also advantageous in view of the possible use of silicone rubber in the light emitting unit 1, as the integrity of the silicone rubber is best maintained when silicone rubber is used with only a minimum of other materials.

A difference between the two metal foils 30 shown in FIGS. 3 and 4 resides in the pattern of the electrically conductive tracks 17. In FIG. 3, the tracks 17 extend between all rows of plates 14, 15, whereas in FIG. 4, the tracks 17 extend only between every other row of plates 14, 15. Hence, with reference to the orientation of the metal foils 30 as shown in the figures, in the structure shown in FIG. 3, the light emitting assemblies 10*a* include horizontal pairs of plates 14, 15, while in the structure shown in FIG. 4, the light emitting assemblies 10*a* include vertical pairs of plates 14, 15. As another consequence, the electrically conductive members 19 connecting the light sources 12, 13 to the electrically conductive tracks 17 of the electric energy distribution arrangement 18 are arranged according to an alternating pattern in a row in the structure shown in FIG. 3, so as to alternately connect adjacent plates 14, 15 in a row to the two tracks 17 extending alongside the row at two sides of the row, while the electrically conductive members 19 are arranged in a consistent pattern in a row in the structure shown in FIG. 4, so as to connect all of the plates 14, 15 in a row to a single track 17 extending alongside the row at one side of the row.

Thus, FIG. 3 shows an arrangement in which each row of light sources is connected alternately to opposite sides of the coils 11*a*, 11*b*. Each column of light sources is connected to the same side of the coils 11*a*,11*b*. FIG. 4 shows an arrangement in which each row of light sources is connected to the same side of the coils 11*a*, 11*b*. Each column of light sources is connected to alternately to opposite sides of the coils 11*a*,11*b*.

The electrically conductive members 19 may be realized in any suitable way, and may comprise wires or tracks, for example. All in all, in the structure shown in FIG. 3, the plates 14, 15 of a column of plates 14, 15 may have the same voltage potential, while in the structure shown in FIG. 4, the plates 14, 15 of a row of plates 14, 15 may have the same voltage potential. Columns or rows of plates 14, 15 having the same voltage potential can be electrically connected to each other, but in the shown example, this is not done in order to have optimal electric redundancy and to offer the highest chance that the light emitting unit 1 can be operated to emit light even in cases of mechanical damage.

The example above makes use of conductivity of the hull, or of a coating such as paint over the hull, to provide the electrical coupling between the capacitors 21, 22.

An alternative is to make use of the conductivity of the sea water in which the marine vessel is submerged.

Figure 5:
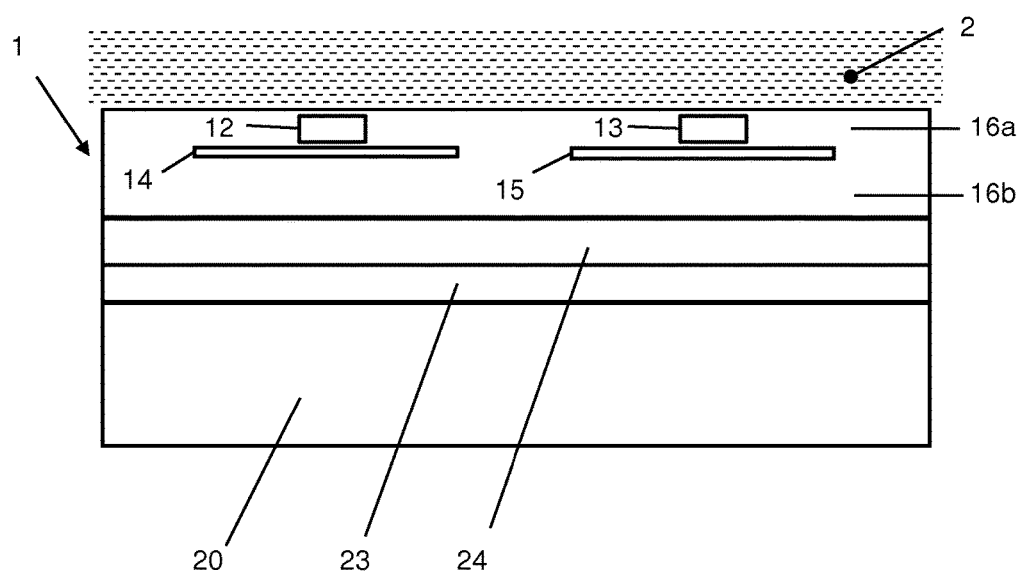
FIG. 5 diagrammatically shows a cross-section of a second example of a light emitting unit according to the invention and a portion of a ship's hull on which the light emitting unit is arranged.

FIG. 5 shows an implementation in which the sea water 2 forms the conductive capacitor terminals. The top dielectric layer 16*a* in this case forms the capacitor dielectric. The light emitting unit 1 is again shown applied over a paint layer 23 and glue layer 24. However, these do not need to be conductive or have particular dielectric properties to meet the required capacitor designs.

In FIG. 5, the light sources 12 are still over the electrically conductive plates 14, 15, and they may again function to reflect light. The top dielectric layer 16a may be thinner than the bottom dielectric layer so that the electrically conductive plates are closer to the sea water than to the hull and/or have a higher permittivity coupling to the water than to the hull.

In an alternative, the electrically conductive plates are at the top of the light emitting element above the light sources, so that they may more easily be placed closer to the sea water than to the hull. The waveguiding design of the slab 16 and/or the design of the electrically conductive plates is such that the electrically conductive plates 14,15 do not prevent light reaching the surface.

Figure 6:
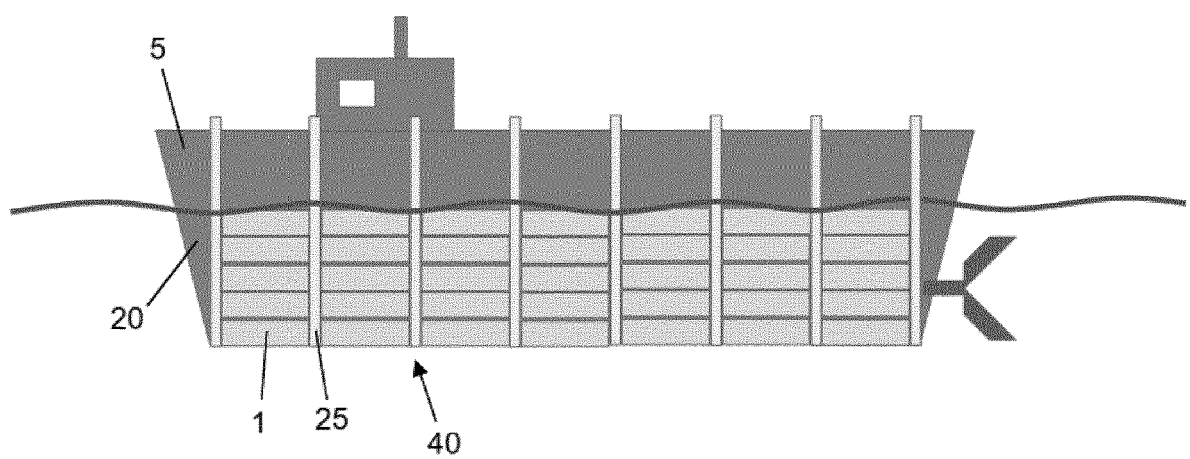
FIG. 6 illustrates how a plurality of light emitting units according to the invention may be arranged on a side of a ship.

FIG. 6 illustrates how a plurality of light emitting units 1 according to the invention may be arranged on a side of a ship 5, and both FIG. 5 and FIG. 6 illustrate how feeding lines 25 can be used for feeding electric energy to light emitting units 1 according to the invention. The ship 5 may be equipped with at least one source of electric power (not shown in the figures), wherein the feeding lines 25 are electrically connected to the at least one source of electric power, and wherein the at least one source of electric power, the feeding lines 25 and the light emitting units 1 constitute a light emitting system 40. In the shown example, the feeding lines 25 extend at positions where the coils 11a, 11b of the light emitting units 1 are located, so that an arrangement of the feeding lines 25 and the light emitting unit 1 is such that inductive transfer of power from the feeding lines 25 to the light emitting unit 1 is enabled. Optionally, thin ferrite plates or foils may be used at the position of the feeding lines 25 to prevent Eddy currents in the metal of the ship's hull 20 and to thereby increase efficiency of energy transfer.

In a practical embodiment, the feeding lines 25 comprise coils 26 which may be fed with a 100-150 kHz sinewave during operation of the light emitting system 40. For the purpose of compensating for capacitive leak current to the hull 20 at the position of the feeding lines 25, the feeding lines 25 may further be provided with a capacitor (not shown), which capacitor may serve as a low pass filter component. This is especially advantageous when high efficiency switched amplifiers are used. In such a case, the capacitor may serve to remove residue of the higher frequency harmonics of the amplifiers. The value of the capacitor in the low pass filter is adjusted with the parasitic capacitance from the feeding lines 25 to the hull 20. A thin ferrite layer (foil) may be applied between the feeding lines 25 and the light emitting units 1 for the purpose of improving efficiency of energy transfer between the coils 26 of the feeding lines 25 and the coils 11a, 11b of the light emitting units 1. All coils 26 of the feeding lines 25 can have the same phase, which contributes to electric redundancy of the light emitting system 40, wherein the light emitting system 40 can still function in its entirety if a feeding line 25 is broken. In that respect, it is practical if the feeding lines 25 are designed to deliver electric power at an increased level of two times a normal level.

An alternative to feeding the primary coils with an AC signal is to use a resonant circuit to generate the AC supply. For example, each feeding line may comprise a resonant circuit, based on a capacitive resonant circuit, with a resonance in the range 60 kHz to 90 kHz.

Generally, the frequency of operation (resonant or driven) may be in the range 50 kHz to 1 MHz, for example 50 kHz to 200 kHz, for example 60 kHz to 90 kHz.

In the shown example, the feeding lines 25 extend in a substantially vertical orientation along the side of the ship 5. That does not alter the fact that within the scope of the invention, any suitable arrangement of feeding lines 25 is possible. In the context of the ship 5, it may be advantageous to use the feeding lines 25 for covering welding seams and/or other surface irregularities of the ship's hull 20.

Figure 8:
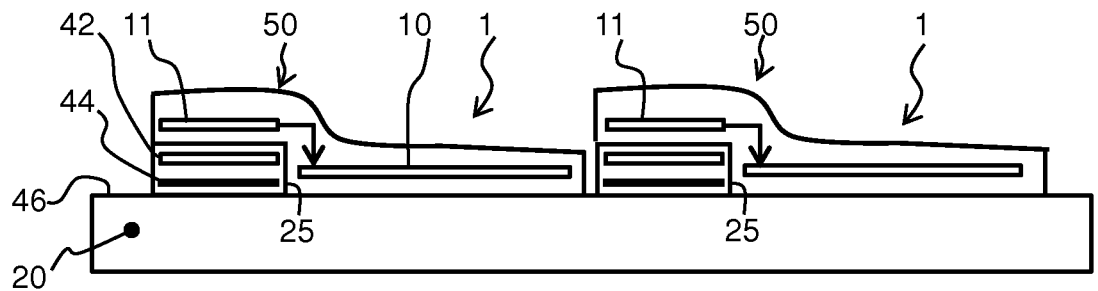
FIG. 8 shows a cross section (in a horizontal plane) through the feeding lines and lighting panels.

FIG. 8 shows a cross section (in a horizontal plane) through the power feeding lines 25 and through the light emitting units 1 (i.e. lighting panels) for an arrangement making use of a metal ship hull. The inductive power transmitters comprise a primary coil 42 and a ferrite sheet 44 between the windings of the primary coil and the metal of the hull 20 of the ship. The surface 46 of the hull is the surface to be protected from fouling. The ferrite sheets 44 prevent Eddy currents in the metal of the ship's hull 20 thereby increasing the efficiency of energy transfer.

In the example shown, the surface 46 is essentially fully covered by the lighting panels. Thus, the surface 46 is protected by the lighting panels 1, and it is the exposed surface of the lighting panels which is vulnerable to fouling. Thus, the lighting provided by the lighting panels aims to prevent the formation of fouling organisms on the surface of the lighting panels.

However, this is still to be understood as forming the system for protecting the hull surface against biofouling (in that without the lighting system, the hull surface will suffer from biofouling).

An alternative arrangement for example may have lighting panels which only cover a small fraction of the surface to be protected, and the light is directed or guided towards the surface to be protected. In such a case, a major part of the hull surface is indeed exposed to water and therefor susceptible to biofouling.

In the example shown in FIG. 8, the inductive power transmitters 42 are mounted against the hull surface 46 and the lighting panels 1 are mounted over the inductive power transmitters.

In particular, an edge region 50 of each lighting panel 1 overlaps the feeding lines 25. The lighting panels 1 each have a secondary coil 11 (as discussed above) located in this edge region, and the light emitting assembly 10 as explained above (and represented in FIG. 8 as a single element, for simplicity) extending between the feeding lines 25.

The secondary windings 11 are aligned with the primary windings 42 to provide inductive power transfer. The wirelessly transmitted power is used by the lighting panels 1 to power the light sources of the light emitting assembly 10.

The primary coils may be formed on or within a printed circuit board of the feeding lines, and the secondary coils may also be formed on or within a printed circuit board of the lighting panel as discussed above.

A flexible printed circuit board of the lighting panels may allow the lighting panels to adapt to the contour of the underlying feeding lines. Instead, there may be separate printed circuit boards in the lighting panel for the coil 11 and for the light emitting assembly and an electrical connection between them.

Figure 9:
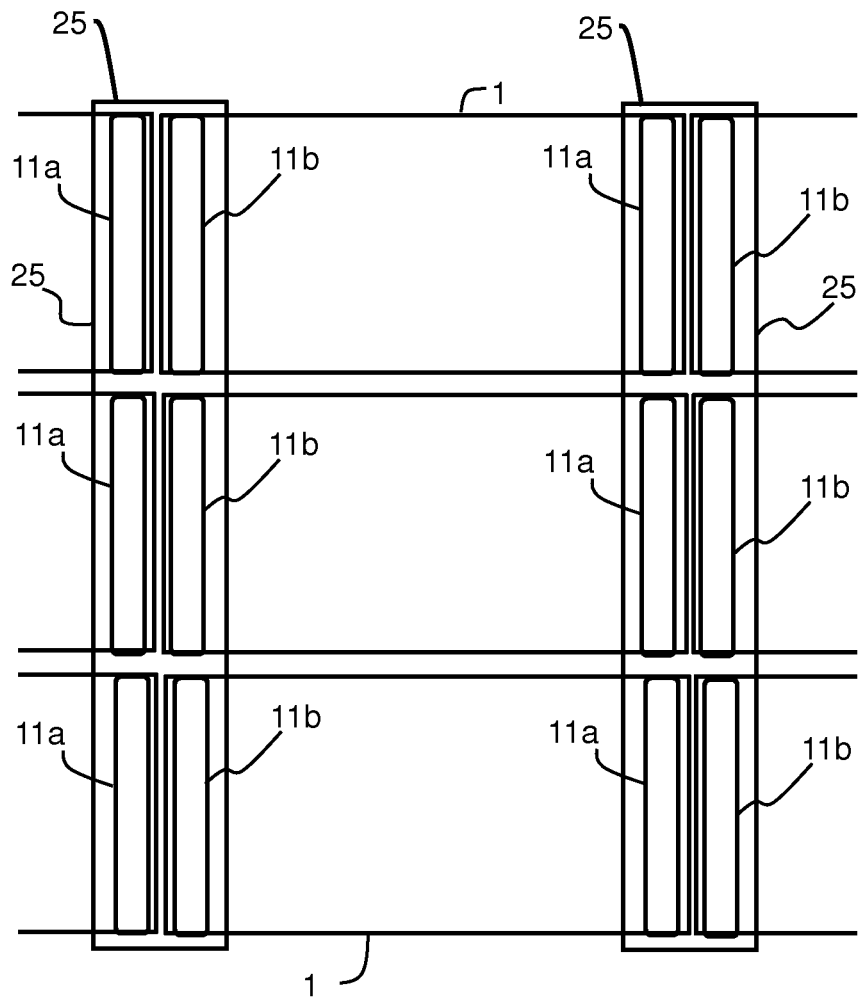
FIG. 9 shows the coil arrangements in more detail.

FIG. 9 shows the coil arrangements in more detail. The lighting panels 1 overlap feeding lines 25 at both lateral edges, and each feeding line 25 has pairs of primary coils arranged along its length. One coil of a pair is for powering a lighting panel 1 to one side and the other coil of the pair is for powering a lighting panel to the other side. In this way, each lighting panel is supplied by power from both sides. This provides redundancy as explained above.

There may for example be between 2 and 50 lighting panels per feeding line 25, for example 20 rows of individual tiles connected to a feeding line.

The light sources of the lighting panels are for example side-emitting UV-C LEDs, wherein the light is emitted primarily from a side of the LED, and more or less parallel to the surface. The optical medium in which the light sources are encapsulated guides at least part of the light emitted from the light sources via total internal reflection through the optical medium. Optical structures may then be provided to disrupt the total internal reflection and scatter light, and then guide the scattered light out of the optical medium towards a target for the light, which is an area where a biofouling organism is present. The optical structures to scatter light may be spread in one or more portions of the optical medium material, possibly throughout all of it, and the light output may be generally homogeneous or else localized.

A biofouling organism on the surface will directly receive the scattered light before it enters the water. Furthermore, some of the scattered light that does enter the water will encounter external scattering sites. This creates illumination within the water, some of which will also reflect back to the surface of the lighting panel where biofouling is to be prevented.

The illumination means that single cell bio-mechanisms at the surface will stop growing and dividing, and will therefore die under influence of the UV-C light.

Internal scattering centers with different structural properties may be combined to provide optical and well as structural characteristics, such as resistance to wear and/or impact. Suitable scatterers comprise opaque objects but largely translucent objects may be used as well, e.g. small air bubbles, glass and/or silica; a requirement is merely that a change in refractive index occurs for the wavelength(s) used.

The principle of light guiding and spreading light over a surface is well-known and widely applied in various fields. Here, the principle is applied to UV light for the purpose of anti-fouling. To maintain the conditions for total internal reflection, the index of refraction of the light guiding material should be higher than that of the surrounding medium.

However, the use of (partly) reflecting coatings on the light guide and/or the reflecting properties of the electrically conductive plates and/or the use of the reflective properties of the protected surface, e.g. the hull of a ship, itself can also be used to establish the conditions for guiding the light through the optical medium.

A number of advantages and aspects of the present invention are summarized in the following.

Figure 7:
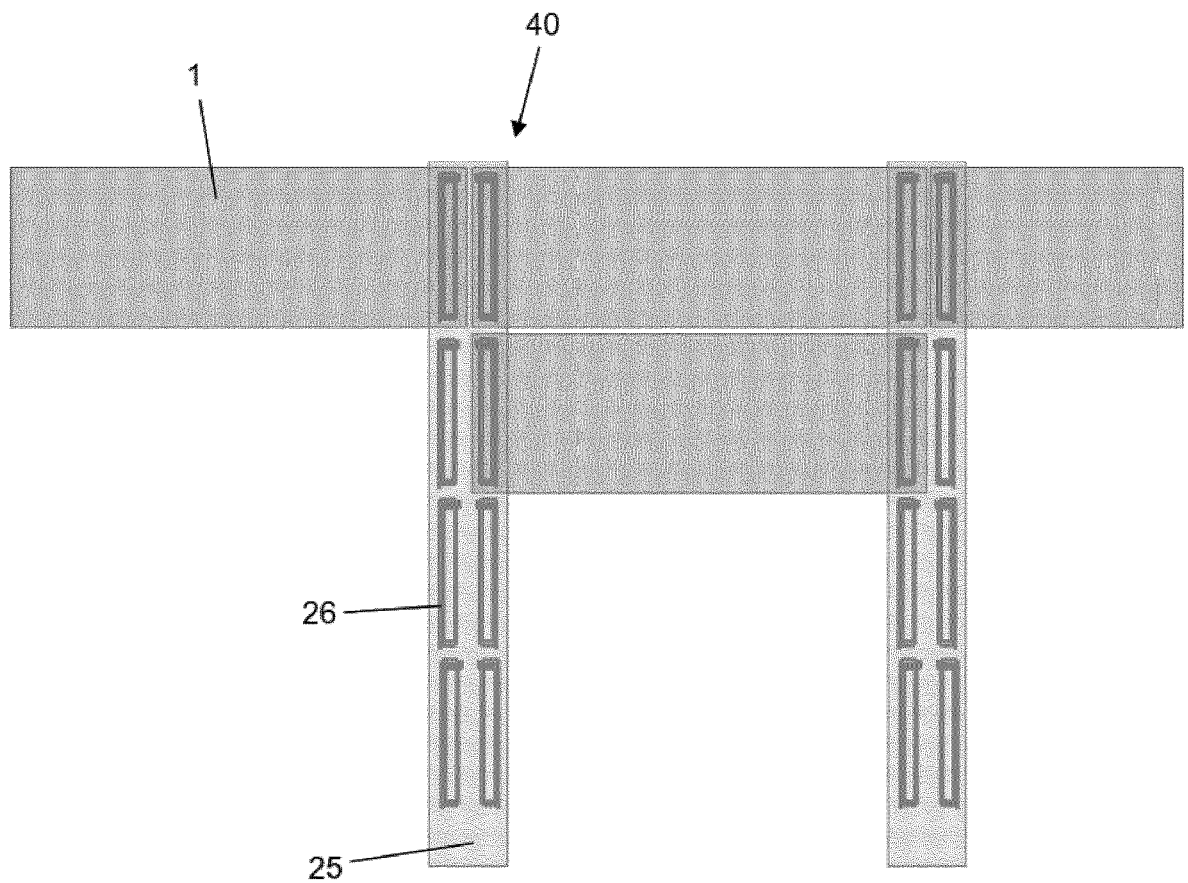
FIG. 7 illustrates how feeding lines can be used for feeding electric energy to light emitting units according to the invention.

The coupling of the light emitting units 1 to electric power supply elements such as the feeding lines 25 shown in FIGS. 6 and 7 is preferably of an inductive nature. Further, the light sources 12, 13 of the light emitting units 1 are in a circuit involving feed of electric energy through capacitors and associated capacitive current limitation. Hence, the light emitting units 1 are fully galvanically isolated. A signal in a range of 100 to 150 kHz is a practical example of a signal that may be used to distribute the electric energy via the electrically conductive surface area of, or over, a marine object (of which a surface area of a ship's hull 20 as referred to in the foregoing is an example). Both resonant and non-resonant operation of the driver are possible within the framework of the invention as explained above. A practical example of a maximum voltage is 48 V, which is considered to be safe.

The light emitting units 1 comprise electrically conductive plates 14, 15 which are used in the feed of electric energy through series capacitors and which may also have a light reflecting function. The plates 14, 15 and components of the electric energy distribution arrangement 18 of the light emitting units 1, such as coils 11a, 11b and electrically conductive tracks 17, may be integrated in a single thin layer/foil/sheet of an electrically conductive material such as metal. In such a configuration, only the lifetime of the light sources 12, 13 matters to the lifetime of the light emitting units 1. Also, the thickness of the light emitting units 1 is mainly determined by the thickness of the light sources 12, 13. As mentioned earlier, the light sources 12, 13 may comprise LEDs. It is preferred if a small as possible LED type is chosen, such as an LED type currently known as nano LED. An example of the electrically conductive material of the thin layer/foil/sheet is aluminum. As can be seen in FIGS. 3 and 4, it is possible to design such a thin layer/foil/sheet with only one crossing 31 per coil 11a, 11b, at the position of which additional thickness is required in order to avoid shorts.

The light emitting units 1 can be manufactured in various ways, wherein the thin layer/foil/sheet of an electrically conductive material may be realized by using material removal techniques or material addition techniques. Further, a plurality of light emitting units 1 may be provided in a mechanically interconnected fashion so as to facilitate a process of applying the light emitting units 1 to a surface area. For example, a string of one or more columns of light emitting units 1 may be wound on a reel or laid down in zigzag fashion on a support.

The light emitting units 1 are intended to be applied to a surface area of a marine object, although the invention could be put to practice in other fields as well. In view of the intended use of the invention, it is desired to have a thin, generally flat design of the light emitting units 1. Also, it is important that the light emitting units 1 and the components involved in supply of electric power to the light emitting units 1 are designed so as to have a high level of electric redundancy as in the context of marine objects, mechanical impacts are likely to take place. In the context of the present text, the term "marine object" is not limited to objects for use in seawater, but is to be understood so as to include objects for use in any type of water that is known to contain biofouling organisms. Examples of marine objects include ships and other vessels, marine stations, sea-based oil or gas installations, buoyancy devices, support structures for wind turbines at sea, structures for harvesting wave/tidal energy, sea chests, underwater tools, etc.

The lighting panels for example have a length (along the horizontal row direction) in the range 1 m to 5 m and a height (along the vertical column direction) in the range 50 cm to 150 cm. For example a small panel dimension may be 600 mm×1200 mm and a large panel dimension may be 1 m×4 m. An example area to be covered, e.g. one side of a ship hull, may be of the order of 100 m length by 10 m height.

It will be clear to a person skilled in the art that the scope of the invention is not limited to the examples discussed in the foregoing, but that several amendments and modifications thereof are possible without deviating from the scope of the invention as defined in the attached claims. It is intended that the invention be construed as including all such amendments and modifications insofar they come within the scope of the claims or the equivalents thereof. While the invention has been illustrated and described in detail in the figures and the description, such illustration and description are to be considered illustrative or exemplary only, and not restrictive. The invention is not limited to the disclosed embodiments. The drawings are schematic, wherein details which are not required for understanding the invention may have been omitted, and not necessarily to scale.

Variations to the disclosed embodiments can be understood and effected by a person skilled in the art in practicing the claimed invention, from a study of the figures, the description and the attached claims. In the claims, the word "comprising" does not exclude other steps or elements, and the indefinite article "a" or "an" does not exclude a plurality. Any reference signs in the claims should not be construed as limiting the scope of the invention.

Elements and aspects discussed for or in relation with a particular embodiment may be suitably combined with elements and aspects of other embodiments, unless explicitly stated otherwise. Thus, the mere fact that certain measures are recited in mutually different dependent claims does not indicate that a combination of these measures cannot be used to advantage.

The term "comprise" as used in this text will be understood by a person skilled in the art as covering the term "consist of". Hence, the term "comprise" may in respect of an embodiment mean "consist of", but may in another embodiment mean "contain/include at least the defined species and optionally one or more other species".

A summary of the invention may read as follows. In the context of anti-biofouling of marine objects, a light emitting unit 1 is configured to be applied to a surface area of a marine object 5 and comprises at least one light source 12, 13 configured to emit anti-fouling light, and two electrically conductive plates 14, 15, wherein the at least one light source 12, 13 is at the one side electrically connected to one of the plates 14, 15 and at the other side to an electric energy distribution arrangement 18 of the light emitting unit 1. The plates 14, 15 are arranged to constitute respective capacitors 21, 22 with an electrically conductive surface area of, or over, a marine object 5, said capacitors 21, 22 being connected in series through the electrically conductive surface area of, or over, the marine object 5 once the light emitting unit 1 is actually applied to the surface area of a marine object 5.

The invention claimed is:

1. A light emitting system for a marine vessel, the system comprising:
    at least one light emitting unit, wherein the at least one light emitting element includes an electric energy distribution arrangement and at least one light emitting assembly having at least one UV-C anti-fouling light source and two electrically conductive plates, and wherein the at least one light emitting assembly is electrically connected to the electric energy distribution arrangement;
    a source of electric power; and
    an electric power supply element, wherein the electric power supply element and the at least one light emitting unit are arranged with respect to each other so as to enable inductive transfer of electric power from the electric power supply element to the at least one light emitting unit,
    wherein a first side of the at least one UV-C anti-fouling light source is electrically connected to one of the electrically conductive plates, and a second side is connected to the electric energy distribution arrangement, and
    wherein the electrically conductive plates are arranged to constitute respective capacitors with an electrically conductive surface formed by or over the surface area of the marine vessel, said capacitors being connected in series through the electrically conductive surface once the light emitting unit is coupled to the surface area of the marine vessel.

2. A light emitting system of claim 1, wherein the electrically conductive surface comprises an electrically conductive surface area of the marine object.

3. The light emitting system of claim 1, wherein the light emitting unit having a thickness smaller than 2 mm.

4. The light emitting system of claim 1, wherein the electric energy distribution arrangement and the at least one light source and the two electrically conductive plates are embedded in a dielectric material.

5. The light emitting system of claim 1, wherein the electrically conductive plate arranged and configured to reflect light emitted by the at least one light source.

6. The light emitting system of claim 1, wherein the at least one light source comprises an LED.

7. An assembly comprising the light emitting system according to claim 1, the assembly further comprising a holder, and a plurality of the at least one light emitting unit, wherein the plurality of light emitting units are mechanically interconnected and arranged on the holder, such that the light emitting units are applied to an electrically conductive surface area of the a marine vessel from the holder.

8. An assembly of comprising the light emitting system of claim 1, the assembly further comprising a marine vessel wherein the electric power supply element and the at least one light emitting unit are positioned on an electrically conductive surface area of the marine vessel.

9. A method of applying a plurality of light emitting units of a light emitting system of claim 1 to an electrically conductive surface area formed by or over the surface area of the marine vessel, the method comprising the step of arranging the light emitting units on the electrically conductive surface area in a pattern of rows and columns.

10. A light emitting system as claimed in claim 1, wherein the light emitting system is attached to the surface of the marine vessel, and the electrically conductive surface comprises a water layer over the surface area of the marine vessel.

11. A light emitting system as claimed in claim 1, wherein the light emitting system is attached to the surface of the marine vessel, and the electrically conductive surface comprises a paint layer over the surface area of the marine vessel.

12. The light emitting system of claim 1, further comprising a layer of electrically conductive material forming the electric energy distribution arrangement and the electrically conductive plates.

13. The light emitting system of claim 12, wherein the layer of electrically conductive material has a thickness between 3-15 µm.

14. The light emitting system of claim 1 wherein each light emitting unit comprises a plurality of light emitting assemblies, each one of the electrically conductive plates of the respective light emitting assemblies are arranged in the light emitting unit in a pattern of rows and columns.

15. The light emitting system of claim 14, wherein the electric energy distribution arrangement comprises electrically conductive tracks extending between the electrically conductive plates of the respective light emitting assemblies.

* * * * *